United States Patent
Ishii et al.

(10) Patent No.: US 10,290,105 B2
(45) Date of Patent: May 14, 2019

(54) MEDICAL IMAGE PROCESSING APPARATUS TO GENERATE A LESION CHANGE SITE IMAGE

(71) Applicant: Toshiba Medical Systems Corporation, Otawara-shi (JP)

(72) Inventors: Hideaki Ishii, Nasushiobara (JP); Shigeharu Ohyu, Yaita (JP); Naotaka Sakashita, Utsunomiya (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 284 days.

(21) Appl. No.: 15/194,015

(22) Filed: Jun. 27, 2016

(65) Prior Publication Data

US 2017/0024888 A1 Jan. 26, 2017

(30) Foreign Application Priority Data

Jul. 23, 2015 (JP) ................. 2015-145626

(51) Int. Cl.
*A61B 5/00* (2006.01)
*G06T 7/00* (2017.01)
*G06T 11/00* (2006.01)
*A61B 5/055* (2006.01)
*A61B 6/03* (2006.01)
*A61B 6/00* (2006.01)

(52) U.S. Cl.
CPC ............ *G06T 7/0016* (2013.01); *A61B 5/055* (2013.01); *A61B 5/4088* (2013.01); *A61B 6/032* (2013.01); *A61B 6/037* (2013.01); *A61B 6/501* (2013.01); *A61B 6/5217* (2013.01); *G06T 11/003* (2013.01); *A61B 6/467* (2013.01); *A61B 6/5235* (2013.01); *A61B 6/563* (2013.01); *G06T 2207/10072* (2013.01); *G06T 2207/30016* (2013.01)

(58) Field of Classification Search
None
See application file for complete search history.

(56) References Cited

U.S. PATENT DOCUMENTS

| | | | |
|---|---|---|---|
| 2005/0244036 A1* | 11/2005 | Rusinek ................ | G06T 7/0012 382/120 |
| 2011/0004092 A1* | 1/2011 | Kato ...................... | A61B 5/055 600/410 |
| 2016/0081575 A1* | 3/2016 | Wu ........................ | G16H 50/30 600/301 |
| 2017/0024888 A1* | 1/2017 | Ishii ...................... | G06T 7/0016 |

FOREIGN PATENT DOCUMENTS

JP 2013-165765 8/2013

* cited by examiner

*Primary Examiner* — Tahmina N Ansari
(74) *Attorney, Agent, or Firm* — Oblon, McClelland, Maier & Neustadt, L.L.P.

(57) ABSTRACT

A medical image processing apparatus according to an embodiment includes processing circuitry and a display. The processing circuitry obtains first imaged data taken of a subject and second imaged data taken of the subject on a date/time different from the date/time on which the first imaged data was taken. The processing circuitry generates estimation data by performing an image processing process that changes the first imaged data on the basis of a predetermined change model. The processing circuitry generates a display image indicating the difference between the estimation data and the second imaged data. The display displays the display image.

16 Claims, 13 Drawing Sheets

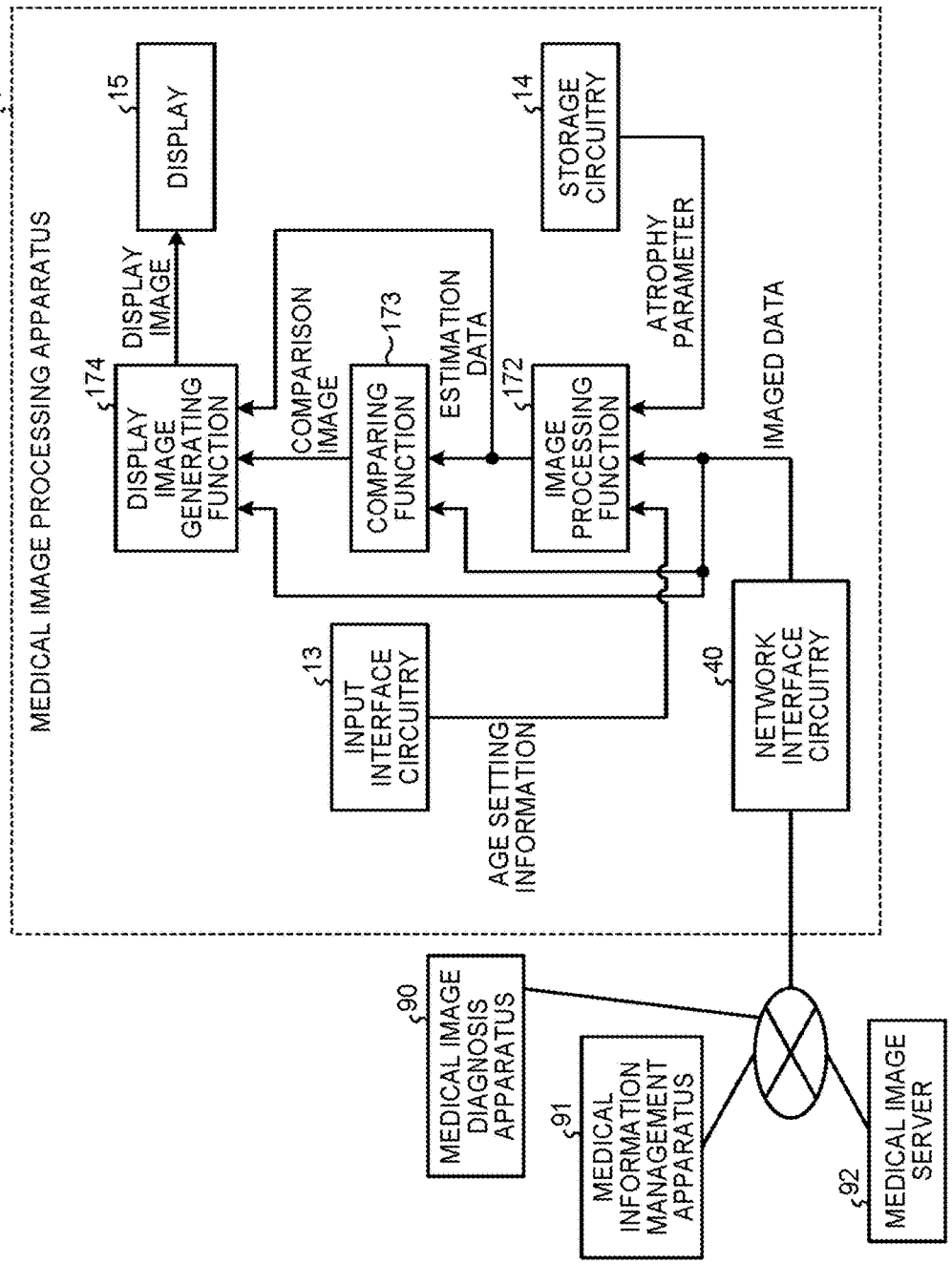

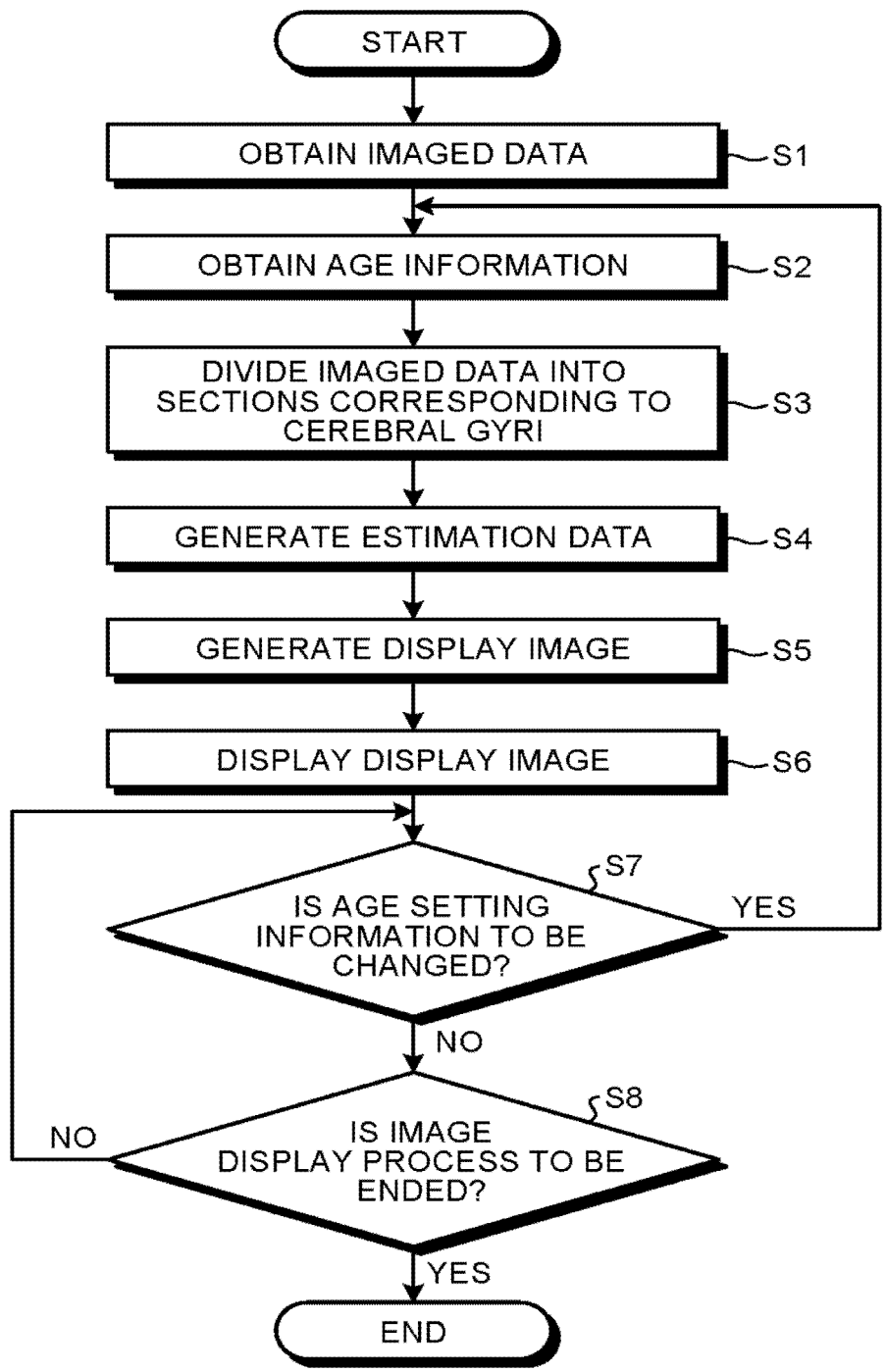

FIG.4A
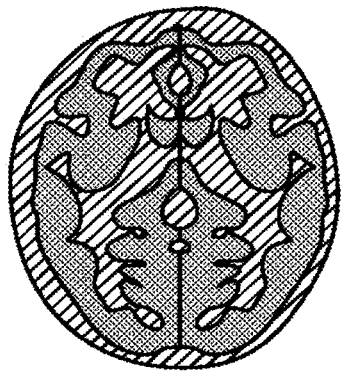
AGE: 20
       161
FIG.4B
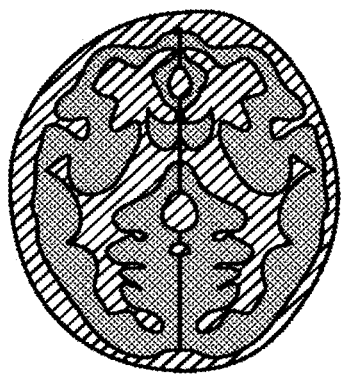
163a    164    163b    162

FIG.4C
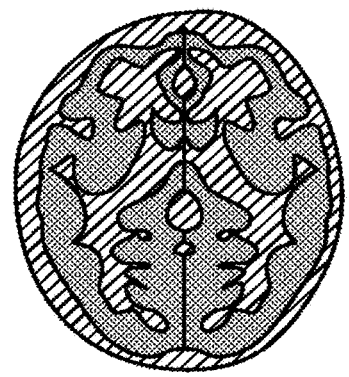
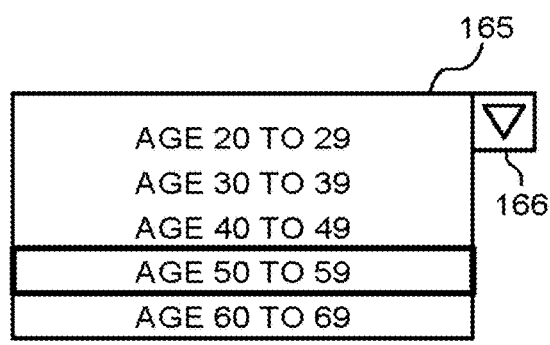
FIG.4D
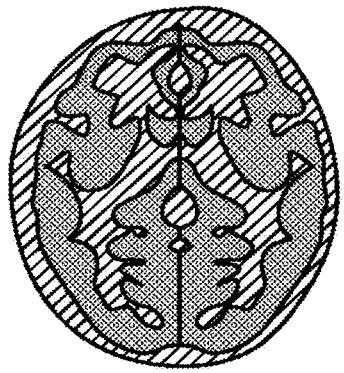

FIG.5A     FIG.5B     FIG.5C

| P1 | P2 | P3 |
|----|----|----|
| P4 | P5 | P6 |
| P7 | P8 | P9 |

| P1 | P2 | P3 |
|----|----|----|
| P4 | P5 | P6 |
| P7 | P8 | P9 |

| P1 | P2 | P3 |
|----|----|----|
| P4 | P5 | P6 |
| P7 | P8 | P9 |

FIG.6

| SUBJECT'S AGE IN ORIGINAL DATA \ SUBJECT'S AGE IN ESTIMATION DATA | AGE 20 TO 29 | AGE 30 TO 39 | AGE 40 TO 49 | AGE 50 TO 59 | AGE 60 TO 69 |
|---|---|---|---|---|---|
| AGE 20 TO 29 |  | 10 | 20 | 35 | 60 |
| AGE 30 TO 39 |  |  | 10 | 25 | 50 |
| AGE 40 TO 49 |  |  |  | 15 | 40 |
| AGE 50 TO 59 |  |  |  |  | 25 |

PART DETERMINED TO BE ATROPHIED

ASSOCIATION AREA/ REGION CONTAINING ATROPHIED PART

FIG.12

| PARAMETERS | | | | | STANDARD DATA | | | | | |
|---|---|---|---|---|---|---|---|---|---|---|
| GENDER | SMOKER | ALCOHOL INTAKE | PHYSIQUE | VITAL DATA | ... | AGE 20 TO 29 | AGE 30 TO 39 | AGE 40 TO 49 | AGE 50 TO 59 | AGE 60 TO 69 | AGE 70 TO |
| MALE | YES | YES | | | | | | | | | |
| MALE | YES | NO | | | | | | | | | |
| MALE | NO | YES | | | | | | | | | |
| MALE | NO | NO | | | | | | | | | |
| FEMALE | YES | YES | | | | | | | | | |
| FEMALE | YES | NO | | | | | | | | | |
| FEMALE | NO | YES | | | | | | | | | |
| FEMALE | NO | NO | | | | | | | | | |

FIG. 13

| GENDER | AGE | PARAMETERS | | | | STANDARD DATA | | | | |
| --- | --- | --- | --- | --- | --- | --- | --- | --- | --- | --- |
| | | TYPE OF TUMOR | STAGE | TREATMENT METHOD | ... | 30 DAYS | 60 DAYS | 90 DAYS | 120 DAYS | ... |
| MALE | AGE 20 TO 29 | | | | | | | | | |
| | AGE 30 TO 39 | | | | | | | | | |
| | AGE 40 TO 49 | | | | | | | | | |
| | AGE 50 TO 59 | | | | | | | | | |
| | AGE 60 TO 69 | | | | | | | | | |
| | AGE 70 TO | | | | | | | | | |
| FEMALE | AGE 20 TO 29 | | | | | | | | | |
| | AGE 30 TO 39 | | | | | | | | | |
| | AGE 40 TO 49 | | | | | | | | | |
| | AGE 50 TO 59 | | | | | | | | | |
| | AGE 60 TO 69 | | | | | | | | | |
| | AGE 70 TO | | | | | | | | | |

MEDICAL IMAGE PROCESSING APPARATUS TO GENERATE A LESION CHANGE SITE IMAGE

CROSS-REFERENCE TO RELATED APPLICATIONS

This application is based upon and claims the benefit of priority from Japanese Patent Application No. 2015-145626, filed on Jul. 23, 2015; the entire contents of which are incorporated herein by reference.

FIELD

Embodiments described herein relate generally to a medical image processing apparatus.

BACKGROUND

Brain images obtained by imaging the brain may be used for making a diagnosis as to whether examined subjects have a disease involving brain atrophy (e.g., Alzheimer's disease, Lewy body dementia, olivopontocerebellar atrophy, or corticobasal degeneration) or as to how much the symptoms have developed. Brains have a tendency of being atrophied by aging, even for healthy people. Thus, it is necessary to differentiate atrophy caused by aging from atrophy caused by a disease, in order to distinguish diseases of the brain. Brain atrophy caused by aging is observed in the whole brain, whereas brain atrophy caused by a disease is observed in a specific part of the brain.

Conventional medical image processing apparatuses evaluate brain atrophy by comparing a standard brain generated on the basis of brain images of healthy people with a brain image of an examined subject.

However, such conventional medical image processing apparatuses perform a non-linear position alignment process by using the generic model called the standard brain. Thus, a problem arises where it is difficult to make a diagnosis accurately, depending on the level of precision of the position alignment process.

BRIEF DESCRIPTION OF THE DRAWINGS

FIG. 2 is a diagram illustrating an exemplary configuration of functional blocks of the medical image processing apparatus according to the embodiment;

FIG. 3 is a flowchart illustrating a procedure from when imaged data is obtained up to when a display image indicating a comparison result is generated according to the embodiment;

FIGS. 4A to 4D are drawings illustrating examples of a Graphical User Interface (GUI) used for inputting or selecting age information according to the embodiment;

FIGS. 5A to 5C are drawings illustrating examples in which an erosion process is applied to a 3-by-3 pixel formation according to the embodiment;

FIG. 6 is a drawing illustrating an example of an atrophy degree table used for determining the number of times the erosion process is to be repeatedly performed according to the embodiment;

FIG. 12 is a table illustrating examples of standard data of brain images corresponding to different pieces of attribute information according to the embodiment; and FIG. 13 is a table illustrating examples of standard data of images taken of lesion sites according to the embodiment.

DETAILED DESCRIPTION

According to an embodiment, a medical image processing apparatus includes processing circuitry and a display. The processing circuitry is configured to obtain first imaged data taken of a subject and second imaged data taken of the subject on a date/time different from a date/time on which the first imaged data was taken. The processing circuitry is configured to generate estimation data by performing an image processing process that changes the first imaged data on a basis of a predetermined change model. The processing circuitry is configured to generate a display image indicating a difference between the estimation data and the second imaged data. The display is configured to display the display image.

Exemplary embodiments to carry out the present disclosure will be explained below.

Figure 1:
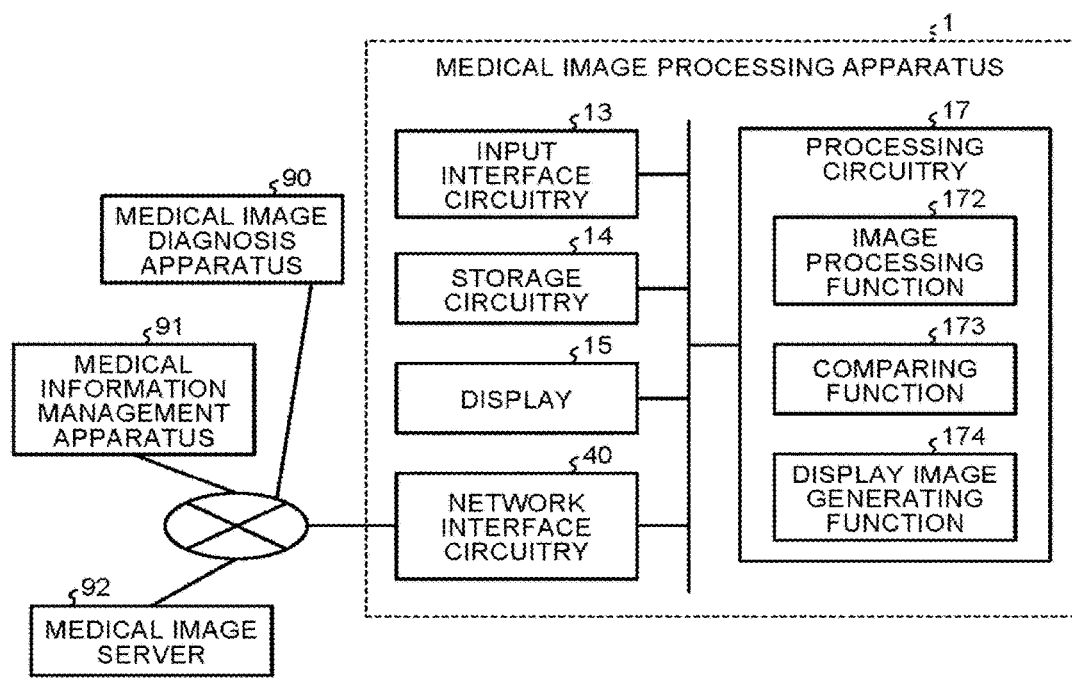
FIG. 1 is a diagram illustrating an exemplary hardware configuration of a medical image processing apparatus according to an embodiment.

FIG. 1 is a diagram illustrating a configuration of a medical image processing apparatus 1 according to an embodiment and also includes other apparatuses and the like that are connected to the medical image processing apparatus 1. The medical image processing apparatus 1 may be, for example, a workstation, an image interpreting viewing tool, or a medical image diagnosis apparatus 90 (explained later).

The medical image processing apparatus 1 has the medical image diagnosis apparatus 90 and a medical information management apparatus 91 connected thereto, via a network 41.

The medical image diagnosis apparatus 90 may be, for example, a Magnetic Resonance Imaging (MRI) apparatus, a Positron Emission Tomography (PET) apparatus, or an X-ray Computed Tomography (CT) apparatus. The medical information management apparatus 91 may be a server included in a Hospital Information System (HIS) or a Radiology Information System (RIS). Network interface circuitry 40 used by the medical image processing apparatus 1 for connecting to the network 41 may be, for example, circuitry that connects to an external device via a wired Local Area Network (LAN) or a wireless LAN.

The medical information management apparatus 91 is an apparatus included in a Hospital Information System (HIS) or a Radiology Information System (RIS) and is configured to manage medical examination order information of subjects including subject information such as a physique, the gender, and the age of each of the subjects as well as imaging condition designation information such as information specifying an imaged site.

A medical image server 92 may be, for example, a Picture Archiving and Communication System (PACS) that obtains and stores therein medical image data compliant with a Digital Imaging and Communication in Medicine (DICOM) standard. The medical image processing apparatus 1 is able to retrieve medical examination images from the past, from the medical image server 92 via a network.

In the present embodiment, an example will be explained in which the medical image diagnosis apparatus 90 is an MRI apparatus. Imaged data generated by the MRI apparatus may be, for example, a T1-weighted image or a T2-weighted image. Because the medical image processing apparatus 1 according to the present embodiment primarily handles brain images of an examined subject (hereinafter, "subject"), the imaged data in the following explanation will refer to images taken of the head of the subject. The imaged data may be volume data which structures a three-dimensional image and of which the smallest unit is a voxel or may be slice data which structures a two-dimensional image and of which the smallest unit is a pixel.

The medical image processing apparatus 1 is configured to obtain the image data of the subject via the network interface circuitry 40. Processing circuitry 17 is configured to generate estimation data from the imaged data, on the basis of information specifying a time series and being input through input interface circuitry 13. The information specifying the time series may be age information, for example. The age information may be a setting value indicating an age or an age group covering a range of ages. Further, the estimation data is image data obtained by estimating imaged data that will be obtained by imaging the brain of a healthy person when the brain has naturally been atrophied due to aging. The estimation data is generated by an image processing function 172. In this situation, the image processing function 172 reads an atrophy parameter from storage circuitry 14 and uses the read atrophy parameter in the image processing process, the atrophy parameter expressing, in the form of an index, how much the brain rendered in the imaged data should be atrophied in the estimation data. The estimation data is compared with the imaged data by a comparing function 173. A display image generating function 174 is configured to output a comparison result as a display image and causes a display 15 to display the display image.

The image processing function 172, the comparing function 173, and the display image generating function 174 are realized with a computer program (hereinafter, "program") that is executable by a processor in the processing circuitry 17. Further, the program is stored either in a storage region incorporated in circuitry of the processor or in the storage circuitry 14. In this situation, the processing circuitry 17 is example of the processing circuitry set forth in the claims.

The term "processor" used in the description of the embodiments refers to a circuit such as, for example, a Central Processing Unit (CPU), a Graphics Processing Unit (GPU), an Application Specific Integrated Circuit (ASIC), or a programmable logic device (e.g., a Simple Programmable Logic Device [SPLD], a Complex Programmable Logic Device [CPLD], or a Field Programmable Gate Array [FPGA]). The processor realizes the functions by reading and executing the program from the storage region incorporated in circuitry of the processor or the storage circuitry 14. Further, as for the processor in the embodiment, the individual processor does not necessarily have to be configured as a single circuit. A plurality of independent circuits may be combined together to structure a single processor so that the functions thereof are realized thereby.

Detailed configurations of functional units of the medical image processing apparatus 1 will be explained below, with reference to FIGS. 2 and 3. FIG. 2 is a functional block diagram of the medical image processing apparatus 1. FIG. 3 is a flowchart illustrating a procedure from when the imaged data is obtained from the medical image diagnosis apparatus 90 or the medical image server 92 connected to the network 41 up to when the display image indicating the comparison result is displayed.

At step S1, the image processing function 172 included in the processing circuitry 17 first obtains the imaged data of the subject. The imaged data is obtained from the medical image diagnosis apparatus 90 or the medical image server 92 via the network interface circuitry 40. Further, when the imaged data is stored in the storage circuitry 14, the imaged data may be read from the storage circuitry 14.

At step S2, the image processing function 172 obtains the age information to generate the estimation data. The age information may be input directly by an operator via the input interface circuitry 13 or may be arranged to be selectable from among candidate values for the age information that are prepared in advance.

The input interface circuitry 13 may be configured with, for example, a mouse, a keyboard, a trackball, a joystick, a press button, a dial, a touch panel, a touch pad, and/or the like. Input information received by the input interface circuitry 13 is either stored in the storage circuitry 14 or transmitted to the functions included in the processing circuitry 17. The input interface circuitry 13 may be configured as a touch panel so as to serve also as the display 15. In this situation, the input interface circuitry 13 is an example of the input circuitry set forth in the claims.

The display 15 is configured with, for example, a liquid crystal display device or a Light Emitting Diode (LED) display device and is configured to display the display image generated by the display image generating function 174 included in the processing circuitry 17. In this situation, the display 15 is an example of the display set forth in the claims.

The storage circuitry 14 is configured with circuitry or the like that writes and reads information to and from a magnetic disk (e.g., a hard disk), a flash memory (e.g., a solid state drive, a Universal Serial Bus [USB] memory, or a memory card), or an optical disk (e.g., a Compact Disk [CD], or a Digital Versatile Disk [DVD]). In this situation, the storage circuitry 14 does not necessarily have to be built into the medical image processing apparatus 1 and may be structured as an external device connected via a USB, for example. In this situation, the storage circuitry 14 is an example of the storage circuitry set forth in the claims.

FIGS. 4A to 4D each illustrate an example of a Graphical User Interface (GUI) that is displayed by the display 15 when the operator either directly inputs or selects the age information via the input interface circuitry 13. The image illustrated above the GUI in each of FIGS. 4A to 4D is a brain image serving as imaged data or estimation data.

FIG. 4A illustrates an example in which a text box 161 is provided into which it is possible to directly input age information. When a numerical value is input to the text box 161 provided on the right side of the word "age", the numerical value is recognized as age information to be reflected into the estimation data. When a numerical value that cannot be reflected in the estimation data is input to the text box 161, the numerical value may be adjusted to a close value or the input may be rejected.

FIG. 4B illustrates an example in which a scroll bar 162 is provided. The buttons each marked with a triangle and positioned on the two ends of the scroll bar 162 are scroll buttons 163a and 163b used for changing the value of the age information. The scroll button 163a positioned on the left has the function of decreasing the value of the age information, whereas the scroll button 163b positioned on the right has the function of increasing the value of the age information. By pressing the scroll buttons 163a and 163b on the left and the right as appropriate, the operator is able to select and change the age information used for the estimation data. Further, in addition to designating the age information by pressing the scroll buttons 163a and 163b on the left and the right, it is also possible to designate the age information by sliding a knob 164 that is provided on the bar between the scroll buttons 163a and 163b on the left and right and is configured to slide to the left and to the right.

FIG. 4C illustrates an example in which candidate values for the age information are displayed in a pull-down list 165. By pressing a pull-down button 166 marked with a triangle, the operator is able to cause the pull-down list 165 to be displayed. From the pull-down list 165 being displayed, the operator selects a value he/she wishes to designate as the age information. In the example illustrated in FIG. 4C, the age groups incremented by ten years of age are displayed as the candidate values for the age information; however, possible configurations are not limited to this example. For instance, it is acceptable to display the candidate values for the age information incremented by one year of age or to display the candidate values for the age information with irregular increments of years of age.

FIG. 4D illustrates an example in which candidate values for the age information are displayed by using radio buttons 167. By selecting one of the radio buttons 167 positioned on the left side of the candidate values for the age information, the operator is able to designate age information. In the example illustrated in FIG. 4D, the age groups incremented by ten years of age are displayed as the candidate values for the age information; however, possible configurations are not limited to this example. For instance, it is acceptable to display the candidate values for the age information incremented by one year of age or to display the candidate values for the age information with irregular increments of years of age.

The image processing function 172 generates the estimation data on the basis of the age information input or selected via any of the GUIs described in the above examples.

At step S3, the image processing function 172 divides the input imaged data into sections corresponding to cerebral gyri.

The cerebral gyri are ridge-shaped sites that are surrounded by one or more sulci corresponding to "wrinkles" of the cerebral cortex. Examples of the cerebral gyri include the parahippocampal gyrus, for example. It is known that the parahippocampal gyrus is found atrophied when Alzheimer's disease occurs.

As a method for dividing the imaged data into the sections corresponding to the cerebral gyri, a template matching process may be used, for example. It is possible to recognize various types of cerebral gyri, by having template shapes of cerebral gyri stored in the storage circuitry 14 in advance and searching for a site in the images in the imaged data that is closest to any of the template shapes. Further, when a process is performed to divide imaged data represented by volume data into sections corresponding to cerebral gyri, for example, templates having three-dimensional information may be prepared or templates corresponding to a plurality of cross-sectional planes in the volume data may be prepared. Further, as the method for dividing the imaged data into sections corresponding to cerebral gyri, it is also acceptable to use another method by which sulci are detected by performing an image processing process so that various types of cerebral gyri are detected on the basis of the positions of the sulci.

The data obtained by dividing the imaged data into the sections corresponding to the cerebral gyri will hereinafter be referred to as cerebral gyrus data.

At step S4, the image processing function 172 applies an atrophying process based on the atrophy parameter read from the storage circuitry 14 to each of the pieces of cerebral gyrus data.

The atrophy parameter is a parameter used in an image processing process in order for the image processing function 172 to determine how much the image of the cerebral gyrus rendered in an input piece of cerebral gyrus data is to be atrophied.

In order for the image processing function 172 to receive the cerebral gyrus data, the age information, and the atrophy parameter as inputs and to output the estimation data corresponding to the predetermined age or age group based on the age information, an atrophy degree table is created, for example. Listed below are two examples of the atrophy parameter that can be registered in the atrophy degree table.

(1) When the number of times an erosion process is to be repeatedly performed is used as the atrophy parameter:

The erosion process is a process by which, with respect to a pixel in an image, the surroundings of the pixel are replaced with pixel values of a background image. By repeatedly performing the process of changing the pixel values in a boundary part of a target region to a value outside of the target region, it is possible to reduce the target region in such a manner that the target region is eroded from the boundary part. The atrophy degree table has registered therein information indicating how many times the erosion process is to be repeatedly performed.

For example, when the image is a black-and-white binary image, to perform the erosion process on a white pixel is, if a black pixel is in the surroundings of the white pixel in question, to change the white pixel in question to a black pixel. FIGS. 5A to 5C are drawings illustrating examples of an image having a 3-by-3 pixel formation, to explain the erosion process. Indexes P1 to P9 are appended to the pixels in FIGS. 5A, 5B, and 5C, for explanation purposes. FIG. 5A is an original image before the erosion process is performed.

In this situation, a pixel P5 positioned at the center of the nine pixels will serve a pixel in question. Among the eight pixels positioned in the surroundings of the pixel P5, the three pixels in total indicated as P1, P2, and P9 are black pixels. Accordingly, the color of the pixel P5 is changed from white to black, and the image illustrated in FIG. 5B is thus obtained. When this procedure is applied to the pixels P3, P4, P6, P7, and P8, which are white pixels, the color of all these pixels is changed to black, except the pixel P7 of which the pixels in the surroundings are all white pixels. As a result, the image illustrated in FIG. 5C is obtained. Because it is possible to repeatedly perform the erosion process, when the erosion process is performed again on the image in which only the pixel P7 is a white pixel as illustrated in FIG. 5C, because the pixels in the surroundings of the pixel P7 are all black pixels, the pixel P7 is changed to a black pixel.

The atrophy degree table is a table indicating how much brain atrophy may progress due to aging for a healthy person and is generated on the basis of standard data, for example. The standard data is data obtained by collecting brain images of a plurality of healthy people, applying a smoothing process or the like to the collected brain images, and putting together a standard brain image for each of different ages or different age groups.

For example, a simulation is carried out to find out how many times the erosion process should repeatedly be performed on the standard data for the age group of 20-29 years old in order to approximate the standard data to the standard data for the age group of 40-49 years old. Subsequently, the number of times the erosion process should repeatedly be performed is registered into the atrophy degree table. FIG. 6 illustrates a table used for determining the number of times the erosion process is to be repeatedly performed, on the basis of a set made up of the age of the subject in the input data on which the erosion process is to be performed and the age of the subject in the estimation data. For example, when cerebral gyrus data for the age group of 40-49 years old is input so as to generate estimation data for the age group of 60-69 years old, it is determined with reference to the atrophy degree table that the erosion process should repeatedly be performed forty times, by referring to the intersection of the row of the age group 40-49 and the column of the age group 60-69.

Figure 7:
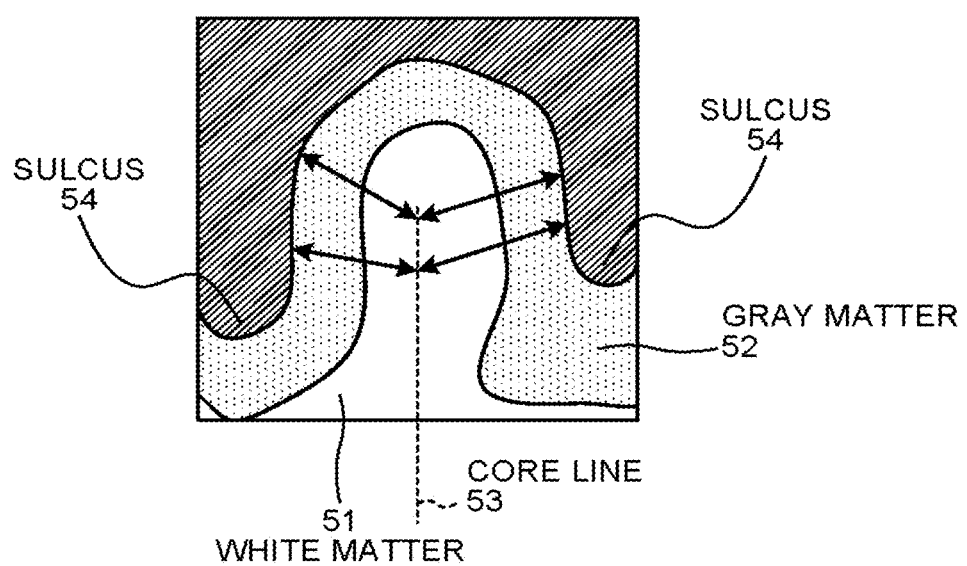
FIG. 7 is a drawing illustrating a cross-sectional plane of a cerebral gyrus taken in a direction substantially orthogonal to the direction in which the sulci extend, according to the embodiment.

(2) When the distance from a core line of a cerebral gyrus to the surface of the cerebral gyrus is used as the atrophy parameter:

FIG. 7 is a drawing illustrating a cross-sectional plane of a cerebral gyrus taken in a direction substantially orthogonal to the direction in which the sulci 54 extend. The tissue on the surface side of the cerebral gyrus is called a gray matter, whereas the tissue positioned on the inside of the gray matter is called a white matter.

A core line 53 of the cerebral gyrus is a line that extends in the protruding direction of the ridge shape on the cross-sectional plane of the cerebral gyrus illustrated in FIG. 7 and that is used as a reference when changing the shape of the cerebral gyrus. For example, the core line 53 of the cerebral gyrus may manually be generated by the operator or may be generated by applying a thinning process to the pixels corresponding to the white matter 51 positioned on the inside of the gray matter 52.

As an index expressing degrees of atrophy, the atrophy degree table uses a rate of change of the distance from the core line 53 to the surface of the cerebral gyrus. For example, a simulation is carried out to find out how much the distance from the core line 53 to the surface of the cerebral gyrus in the standard data for the age group of 20-29 years old needs to be decreased in order to approximate the standard data to the standard data for the age group of 40-49 years old, so that the degree of decrease (e.g., a percentage value) obtained in this manner is registered into the atrophy degree table. On the basis of a set made up of the age of the subject in the cerebral gyrus data on which the atrophying process is to be performed and the age of the subject in the estimation data, the table used for determining the degree of decrease in the distance from the core line 53 to the surface of the cerebral gyrus can be generated by replacing the number of times the erosion process needs to be performed illustrated in FIGS. 5A to 5C with the degrees of decrease. The values that can be used as the atrophy parameter are not limited to the rate of change of the distance from the core line 53 to the surface of the cerebral gyrus. It is also acceptable to use, for example, a rate of change of the distance from the core line 53 to an arbitrary point on the inside of the gray matter 52.

The two types of atrophy parameters have thus been explained; however, the values that can be registered in the atrophy degree table are not limited to these examples. For instance, the degree of decrease in the number of pixels corresponding to the gray matter contained in an image from the cerebral gyrus data may be used as an atrophy parameter. It is possible to obtain the atrophy parameter by extracting the pixels corresponding to the gray matter and calculating the degree of decrease in the number of pixels. It is possible to extract the gray matter and the white matter separately from each other by, for example, setting a threshold value for either the pixel values or the brightness values of the cerebral gyrus data. It is possible to calculate the degree of decrease in the number of pixels corresponding to the gray matter by, for example, calculating the difference in the number of pixels or calculating a decreasing percentage in the number of pixels between before and after the atrophying process.

The atrophy degree table explained above does not necessarily have to be generated by the medical image processing apparatus 1 of the present embodiment. The atrophy degree table may be generated in advance by an apparatus different from the medical image processing apparatus 1. The atrophy degree table generated in advance may be stored in the storage circuitry 14 included in the medical image processing apparatus 1, so that the image processing function 172 is able to read and use the table for the atrophying process, as appropriate.

The atrophy parameter used by the image processing function 172 to generate the estimation data does not necessarily have to be obtained by referring to the atrophy degree table. Alternatively, it is possible to generate a mathematical function used for calculating the atrophy parameter by using the age of the subject in the cerebral gyrus data on which the atrophying process is performed and the age of the subject in the estimation data as variables, while deriving an approximate formula from the standard data.

In the present example, the atrophy parameter stored in the parameter degree table may be a combination of a plurality of types of atrophy parameters. Further, the atrophy degree table and the mathematical function used for calculating the atrophy parameter may be used in combination. Furthermore, the atrophy parameter may be generated by combining imaged data of the subject from the past in a healthy state with the standard data. The information about the age or the age group of the cerebral gyrus data to be input may be read from information appended to the cerebral gyrus data or the imaged data before being divided into the sections corresponding to the cerebral gyri or may be input by the operator via the input interface circuitry 13.

At step S5, the display image generating function 174 generates a display image by using the estimation data generated by the image processing function 172. Further, the display image is not limited to an image displaying the estimation data together with the imaged data. The display image may be a comparison image that is generated by the comparing function 173 included in the processing circuitry 17 and that highlights the difference between the imaged data and the estimation data. Further, when the imaged data is three-dimensional volume data, the estimation data and the comparison image may be displayed three-dimensionally or may be displayed on an arbitrary cross-sectional plane.

Next, display images each containing the estimation data generated by the display image generating function 174 will be explained below by using examples (a), (b), and (c).

Figure 8A:
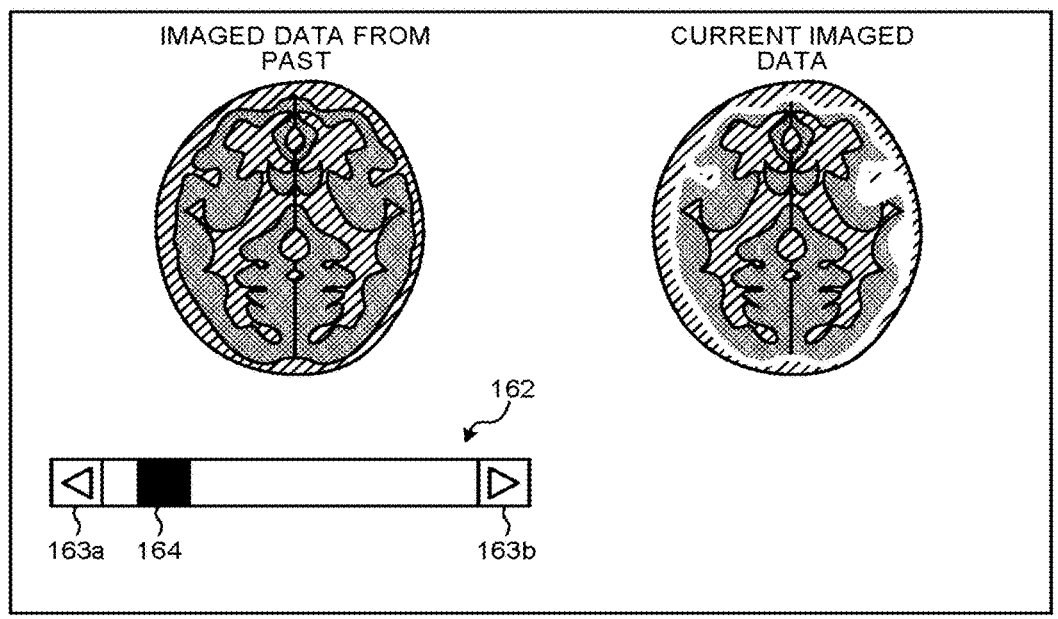
FIGS. 8A and 8B are drawings illustrating display images according to the embodiment in which imaged data from the past and estimation data are each arranged side by side with current imaged data.
Figure 8B:
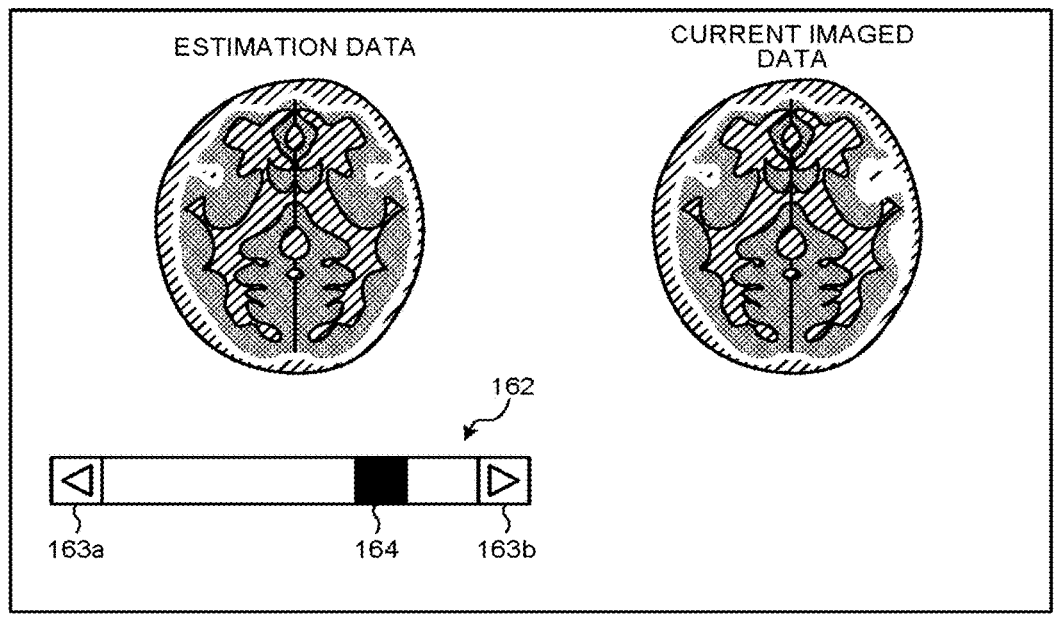

(a) A display image in which the estimation data and the actual imaged data of the subject are displayed side by side:

FIGS. 8A and 8B are drawings illustrating display images in which two pieces of imaged data are displayed side by side. FIG. 8A illustrates a display image in which imaged data of the subject taken in the past is displayed together with current imaged data of the subject. Underneath the imaged data from the past, the scroll bar 162 is displayed, which is a GUI used for setting the age information via the input interface circuitry 13. When the knob 164 of the scroll bar 162 is slid to the right, estimation data based on the imaged data reflecting the time lapse corresponding to the position of the knob 164 will be displayed above the scroll bar 162. FIG. 8B illustrates a display image in which the estimation data generated as a result of sliding the knob 164 is arranged side by side with the current imaged data.

In the present example, a comparison is made between the estimation data and the current imaged data; however, the current imaged data is merely an example of what can be compared with the estimation data. Accordingly, a comparison may be made with imaged data taken at a point in time in the past, instead of with the current imaged data. Further, when there are a plurality of pieces of imaged data of the subject over a time period in the past, it is also acceptable to configure the display image in such a manner that the pieces of imaged data that were actually taken are switched from one to another, in conjunction with changes in the age information for the estimation data.

As explained above, it is possible to view the estimation data arranged side by side with the imaged data taken at the age or the age group that is set when generating the estimation data. The display image is therefore helpful in searching for atrophy occurring in a lesion site.

Figure 9A:
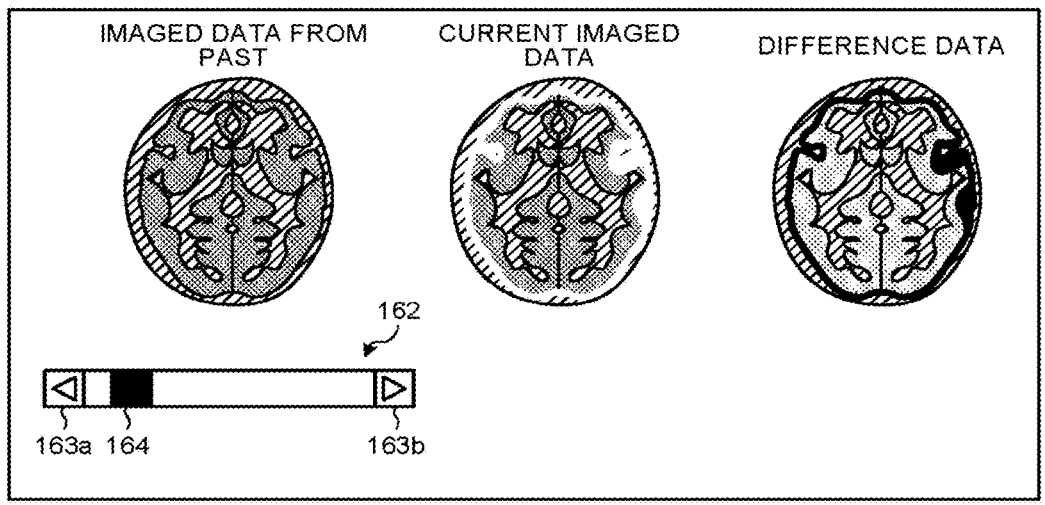
FIGS. 9A and 9B are drawings illustrating display images according to the embodiment in which imaged data from the past and estimation data are each arranged side by side with current imaged data and difference data.
Figure 9B:
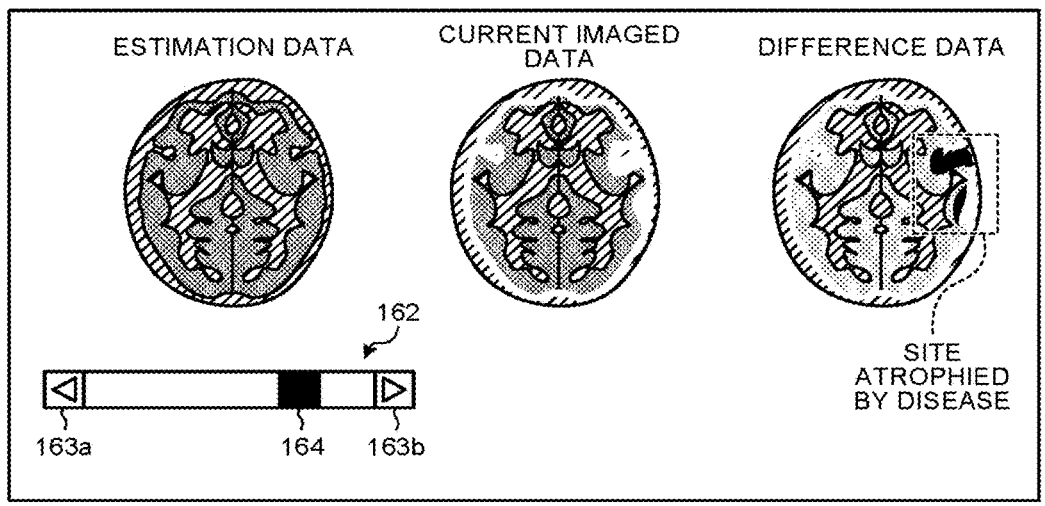

(b) A display image displaying difference data between the estimation data and the current imaged data:

FIGS. 9A and 9B illustrate examples of display images in each of which three pieces of image data are displayed side by side. FIG. 9A illustrates a display image displaying imaged data from the past, current imaged data, and difference data generated by the comparing function 173 to indicate the difference between the imaged data from the past and the current imaged data. Underneath the imaged data from the past, the scroll bar 162 is displayed, which is a GUI used for setting the age information via the input interface circuitry 13. When the knob 164 of the scroll bar 162 is slid to the right, estimation data reflecting the time lapse corresponding to the position of the knob 164 is displayed above the scroll bar 162, as illustrated in FIG. 9B. When the age information for the estimation data is changed, the difference data is also updated. In the difference data in FIG. 9A, the region displayed as being highlighted is observed in the entirety of the imaged data.

FIG. 9B illustrates the display image displaying the difference data between the estimation data generated under the condition of the same age information as that of the current imaged data and the current imaged data. In this difference data, the atrophied parts that naturally occur due to aging do not appear as the difference, but the atrophied sites caused by a disease, which are significantly atrophied locally, are displayed in a highlighted manner.

The difference data output by the comparing function 173 may be displayed by varying the colors in accordance with the magnitude of the differences in the pixel values or the brightness values of the pixels. For example, the difference data may be displayed in colors closer to red as the difference increases and may be displayed in colors closer to blue as the difference decreases. Further, the magnitude of the differences may be expressed by using different levels of darkness of a color.

In the present example, the difference data is generated by using the estimation data and the current imaged data. However, the current imaged data is merely an example of images that can be used for generating the difference data. Accordingly, imaged data taken at a point in time in the past may be used instead of the current imaged data.

As explained above, because the estimation data, the actual imaged data, and the difference data indicating the difference therebetween are displayed, it is possible to easily recognize the atrophied sites caused by a disease.

(c) A display image containing a comparison image obtained by using a warp field based on the estimation data:

When two mutually-different images are taken of a single subject, and a position alignment process is anatomically performed on the two images, a vector field that indicates a change in the position of any anatomically-same point is called a warp field. In the present embodiment, a change in the position of any tissue that is considered to be anatomically the same between imaged data on which the atrophying process is to be performed and the estimation data is calculated as a vector, for each of the voxels or for each of the grids obtained by dividing the image into sections of an appropriate size. The vector field which is represented by a set of the calculated vectors is the warp field. In the warp field, the higher the degree of atrophy is, the larger is the vector. Accordingly, when generating the warp field, it is possible to express how much atrophy is caused in which site, by using colors corresponding to the sizes of the vectors to render the voxels, which are the smallest units for which the vectors can be generated, or to render the grids obtained by dividing the image into sections of an appropriate size.

Figure 10:
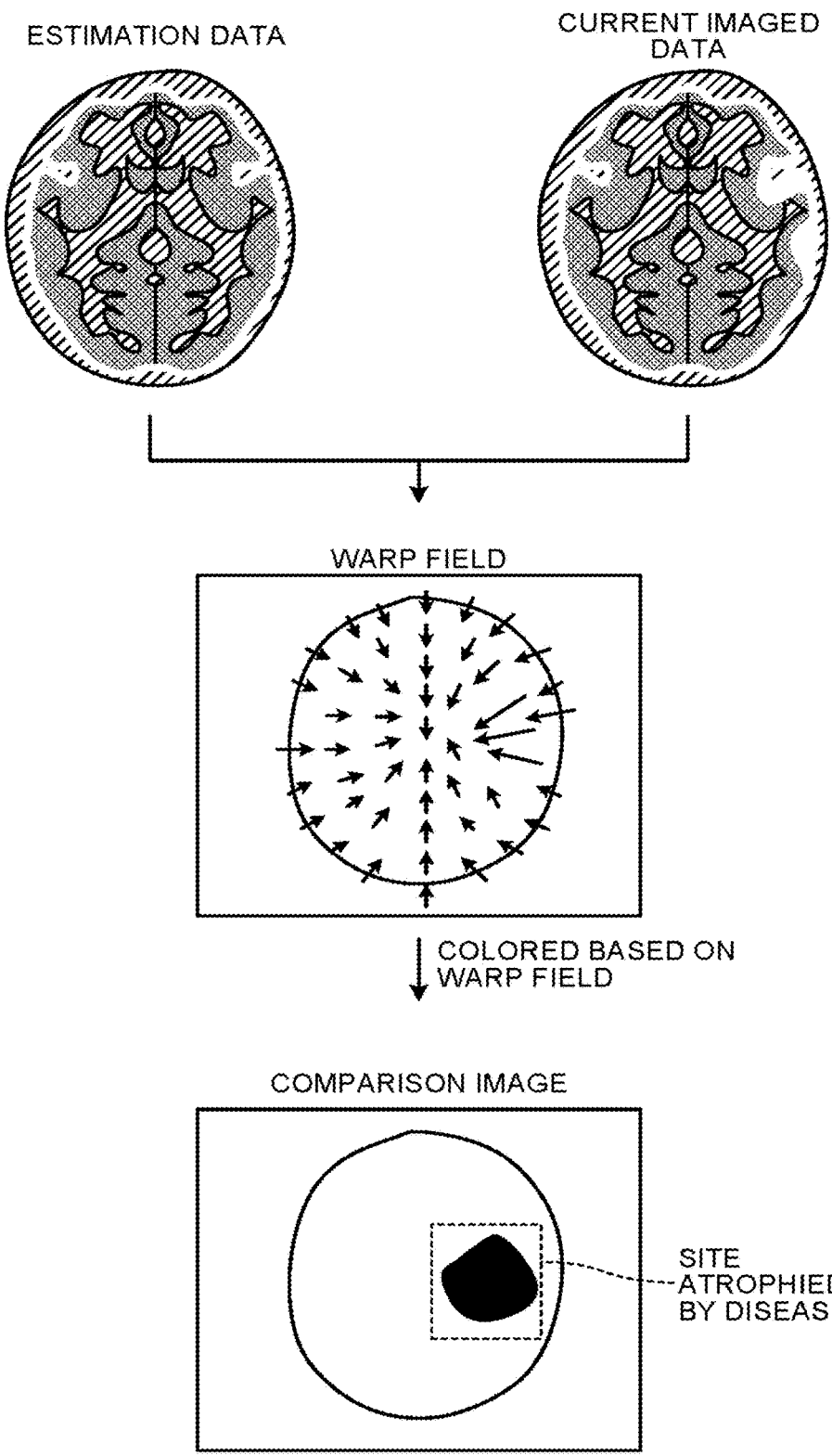
FIG. 10 is a chart for explaining a procedure of generating a display image for displaying an atrophied site by using a warp field according to the embodiment.

FIG. 10 is a chart illustrating an overview of a procedure of generating a display image displaying an atrophied site by using a warp field. First, the comparing function 173 performs an anatomical position alignment process on the estimation data and the current imaged data, so as to generate a warp field, which is a vector field. Further, for example, the comparing function 173 generates a comparison image that is colored according to the sizes of the vectors in the warp field. In the comparison image illustrated in FIG. 10, because larger vectors are present in the right middle part of the warp field used as a base, the right middle part is indicated with a darker color in FIG. 10. To indicate the distribution of sizes of the vectors, it is possible to express the distribution using different colors, instead of using the different levels of darkness of a color.

As for modes of the display image, for example, the display image may be in such a mode in which the image of the difference data in FIG. 9A or 9B is replaced with an image displaying the atrophied site in a highlighted manner by using the warp field.

In the present example, the warp field is generated by using the estimation data and the current imaged data so as to generate the display image displaying the atrophied site in the highlighted manner on the basis of the sizes of the vectors in the warp field. However, the current imaged data is merely an example of images that can be used for generating the difference data. Alternatively, imaged data taken at a point in time in the past may be used for generating the warp field.

As explained above, because the display image is displayed in which the atrophied site is displayed in the highlighted manner on the basis of the sizes of the vectors in the warp field, it is possible to easily recognize the atrophied site caused by a disease.

In the examples (a) to (c) explained above, the scroll bar 162 is displayed as the GUI used for setting the age information for the estimation data; however, possible embodiments are not limited to these examples. It is also acceptable to use the text box 161, the pull-down list 165, and the radio buttons 167 illustrated in FIGS. 4A, 4C, and 4D and/or the like.

Further, in the examples (a) to (c) explained above, the morphological image indicating the shape of the brain in the two-dimensional image is used as the display image; however, possible embodiments are not limited to these examples. For instance, when the imaged data is three-dimensional volume data, difference data may be displayed to indicate a volume difference expressing the atrophy of the brain viewed from the exterior or a region density difference expressing the atrophy of the brain while taking into account the degree of density/sparsity on the inside of the brain that is not visible from the outside.

At step S6, the display image generated by the display image generating function is displayed by the display 15.

At step S7, it is judged whether the age information applied to the estimation data is to be changed or not. When the age information is not to be changed, the process proceeds to step S8. On the contrary, when the age information is to be changed, the process returns to step S2.

At step S8, the medical image processing apparatus 1 is in a state of waiting for an input where it is judged whether the display of the display image by the display 15 is to be ended or not according to an input from the operator. When the image display is to be continued, the process returns to step S7. When the image display is to be discontinued, the flow is ended.

At steps S3 and S4 in the flow described above, the example is explained in which the atrophying process based on the atrophy parameter is performed on the cerebral gyrus data obtained by dividing the input imaged data into the sections corresponding to the cerebral gyri. However, the method for performing the atrophying process is not limited to this example. It is also acceptable to perform the atrophying process based on the atrophy parameter on the whole imaged data that is not divided, instead of each of the pieces of cerebral gyrus data.

In the examples (a) to (c) of the display images generated by the display image generating function 174, the part determined to be atrophied is simply displayed in the display image at step S5 in the flow explained above. However, possible embodiments are not limited to these examples. In a modification example described below, the display image displays which sites in terms of clinical divisions of the brain, the atrophied site corresponds to.

Modification Examples

Figure 11A:
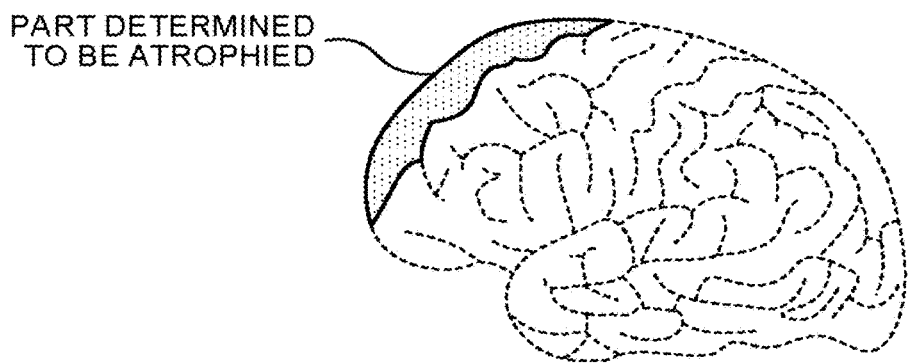
FIGS. 11A, 11B, and 11C are drawings illustrating display images used for displaying atrophied sites together with a cerebral map according to the embodiment.

First, the comparing function 173 judges whether there is any atrophied site in the imaged data, by comparing the imaged data with the estimation data generated by the image processing function 172. FIG. 11A is a drawing illustrating a brain image viewed from a side of the head. The shaded part in FIG. 11A is a site determined by the comparing function 173 to be atrophied.

Figure 11B:
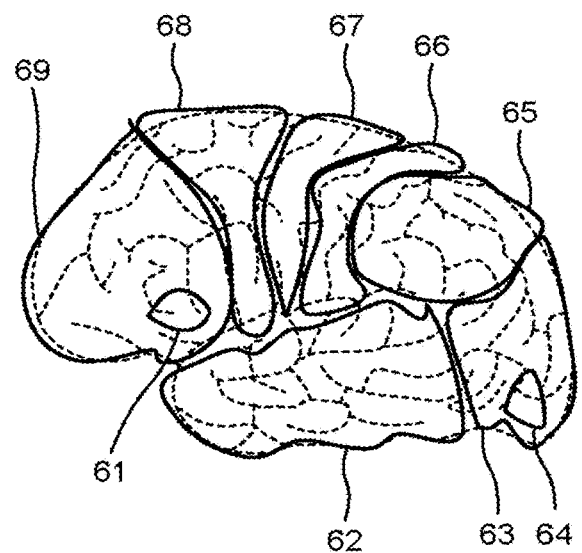

Subsequently, the comparing function 173 combines the image indicating the atrophied site illustrated in FIG. 11A with a brain map indicating clinical divisions of the brain illustrated in FIG. 11B. FIG. 11B illustrates an example of the brain map. For example, the brain map indicates the divisions with association areas and areas such as the Broca's area 61, a temporal association area 62, an occipital association area 63, a visual area 64, a parietal association area 65, a somatosensory area 66, a motor area 67, a motor association area 68, and a frontal association area 69.

Figure 11C:
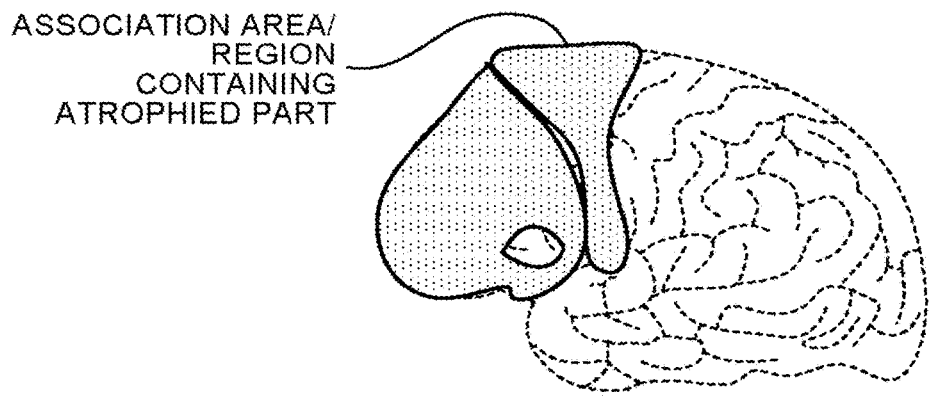

Further, as illustrated in FIG. 11C, the comparing function 173 highlights the parts of the brain map containing the atrophied site by shading the parts in the combined image. In the example illustrated in FIG. 11C, two or more of the association areas and areas contain the atrophied site. More specifically, the part determined to be the atrophied site is present in both the motor association area 68 and the frontal association area 69. Thus, the two association areas are displayed in a highlighted manner.

Because the human body functions that are relevant to the association areas and the areas are clinically known, it is possible to visually recognize the relevance between the atrophied site and the human body functions.

The brain map indicating divisions does not necessarily have to indicate divisions with the association areas and the areas as illustrated in FIG. 11B. For instance, a brain map may be divided according to cerebral lobes.

Further, the method for highlighting the parts of the brain map containing the atrophied site as illustrated in FIG. 11C is not limited to shading the parts. For example, it is acceptable to display the parts in a highlighted manner by using different colors, different levels of darkness, or different levels of transparency. Further, it is also acceptable to display only the outline of each of the parts of the brain map in a highlighted manner. Furthermore, it is also acceptable to display, in a highlighted manner, how much percent of each of the parts in the brain map is accounted for by the region determined to be the atrophied site, by using different colors or different levels of darkness. In order to highlight the parts in the brain map containing the atrophied site, while displaying at the same time how much percent of each of the parts in the brain map is accounted for by the region determined to be the atrophied site, for example, whether each of the parts contains the atrophied site or not is indicated by being colored or not, whereas the percentage of the atrophied site in each of the parts of the brain map is expressed by using different levels of darkness of the color or different levels of brightness.

According to the embodiment described above, the image processing function 172 generates the estimation data by changing the shape of the imaged data of the subject to be observed. For example, on the basis of the atrophy parameter obtained with reference to the standard data or the imaged data from the past, the image processing function 172 performs the atrophying process on the imaged data. As a result, it is possible to precisely estimate the image of the atrophied brain corresponding to the time when the observed subject has aged while staying healthy. Further, because it is possible to generate the estimation data with excellent precision, it is possible to generate the display image in which only the site atrophied by a disease is highlighted, when the difference data between the imaged data of the subject and the estimation data is calculated. Individual differences in the shape of the brain among subjects make a smaller impact on the level of precision of the atrophy detecting process, compared to conventional examples where an atrophied site is identified by aligning the position of the imaged data of an observed subject with the standard brain. In addition, because it is possible to generate the display image highlighting only the site atrophied by a disease, it is possible to find atrophy caused by diseases at an early stage.

Further, to generate the estimation data, the image processing function 172 divides the imaged data into the sections corresponding to the cerebral gyri and performs the atrophying process on each of the cerebral gyri. While brain atrophy due to aging spreads all over the brain, brain atrophy caused by a disease tends to occur locally. Thus, by performing the atrophying process on each of the cerebral gyri, it is possible to arrange the estimation data to reflect changes in the shape according to tendencies of atrophy in each lesion site.

In the display image generated by the display image generating function 174, the atrophied site of the brain is expressed by using different levels of darkness of a color or different colors. With this arrangement, it is possible to recognize the atrophied site of the brain, and further, the site atrophied by a disease, with excellent level of visual recognizability.

Further, the display image generating function 174 is able to display the atrophied site of the brain in the highlighted manner for each of the regions in the brain map. The brain map indicates the divisions of the brain with the association areas and the areas or the cerebral lobes, and the human body functions governed by each of the divisions are clinically known. Accordingly, by observing which region of the brain map is atrophied, it is possible to determine which function of the human body is disabled or may be disabled.

<The Standard Data>

In the embodiment described above, the example is explained in which the standard data corresponding to each of the age groups is generated on the basis of the brain images of the age group. However, possible embodiments are not limited to this example. It is also acceptable to generate standard data that is finely classified on the basis of attribute information of individual persons. For example, it is possible to use big data that realizes a unitary management system by integrating medical images and various types of databases together for categorizing subjects from whom the brain images are acquired into groups according to attribute information thereof and generating standard data corresponding to age groups for each of different pieces of attribute information. In one example, the subjects from whom the brain images are acquired are categorized into groups according to attribute information thereof such as residing areas, ethnic groups, vital data, lifestyle habits, and the like. Further, the standard data is generated by putting brain images together for different ages or for different age groups, in correspondence with the different pieces of attribute information.

FIG. 12 is a table illustrating examples of standard data of brain images corresponding to different pieces of attribute information according to the embodiment. For example, as illustrated in FIG. 12, the standard data is generated in correspondence with attribute information including gender, physique, lifestyle habits (smoking, alcohol intake, etc.) vital data, and the like. In this situation, the vital data is, for example, data including information such as body temperatures, blood pressure levels, pulse rates, blood flow descriptions, and the like. In other words, the vital data is data indicating the levels of body temperature, blood pressure, and pulse in a normal state and how the blood vessels and the blood flows are. Further, the physique is indicated by, for example, a height and a weight or a Body Mass Index (BMI) value.

For example, as illustrated in FIG. 12, the standard data corresponding to the attribute information is generated by acquiring brain images of each of the age groups, in correspondence with the pieces of attribute information including the gender, whether the subject is a smoker or not, whether the subject consumes alcohol or not, the physique, and the vital data. In other words, to generate the standard data corresponding to the attribute information, the brain images of a plurality of subjects are categorized into groups in correspondence with the pieces of attribute information of the subjects and are further categorized into the age groups. After that, as a result of a smoothing process applied to the brain images categorized into the age groups, extreme components in the brain images are smoothed. Further, as a result of a statistical process applied to the brain images categorized in the age groups resulting from the smoothing process, the standard data indicating a standard brain image (e.g., an average brain image) of each of the age groups corresponding to each of the different pieces of attribute information is generated. To generate the standard data corresponding to each of the different pieces of attribute information, standard data for each of the age groups is generated for each of the different pieces of attribute information.

In this situation, the standard data corresponding to the attribute information illustrated in FIG. 12 is generated in correspondence with, for example, residing areas of the subjects, ethnic groups of the subjects, or ethnic groups in each of the residing areas of the subjects. Further, on the basis of the standard data corresponding to the age groups generated in this manner, an atrophy parameter is calculated in correspondence with each of the pieces of attribute information, so as to generate an atrophy degree table corresponding to each of the pieces of attribute information. In one example, an atrophy degree table is generated by calculating an atrophy parameter from the standard data for the different age groups corresponding to attribute information such as "residing area: A; ethnic group: B; gender: male; smoker: Yes; alcohol intake: Yes; physique (BMI): a; blood pressure: b; and blood flow: c". Similarly, another atrophy degree table is generated in correspondence with attribute information such as "residing area: A; ethnic group: B; gender: male; smoker: Yes; alcohol intake: Yes; physique (BMI): a; blood pressure: b; and blood flow: d".

In this situation, as for the attribute information indicated with numerical values such as the physique and the vital data, it is also acceptable to set a number of ranges for each of these pieces of attribute information, so as to categorize the attribute information according to the ranges. For example, when "BMI" values are used for the physique, it is acceptable to set six ranges such as "lower than 18.5" "18.5 or higher but lower than 25.0", "25.0 or higher but lower than 30.0", "30.0 or higher but lower than 35.0", "35.0 or higher but lower than 40.0", and "40.0 or higher", so as to categorize the physiques of the subjects into these six ranges.

In this situation, in the atrophy degree tables described above also, it is acceptable to use the number of times the erosion process is to be repeatedly performed or the distance from the core line of the cerebral gyrus to the surface of the cerebral gyrus as an atrophy parameter. Further, the atrophy degree tables described above may be generated by the medical image processing apparatus 1 by using the brain images and the attribute information of the subject obtained via the network 41 and may be stored in the storage circuitry 14. In other words, the processing circuitry included in the medical image processing apparatus 1 may generate the standard data corresponding to the attribute information by using the brain images and the attribute information and may generate the atrophy degree tables on the basis of the generated standard data. Alternatively, the atrophy degree tables may be generated by the medical information management apparatus 91, obtained by the medical image processing apparatus 1 via the network 41, and stored in the storage circuitry 14. Further, the atrophy parameters and the atrophy degree tables may be updated as appropriate, when the databases in the big data are updated.

The processing circuitry 17 included in the medical image processing apparatus 1 is configured to perform the image processing process that renders atrophy caused in a region corresponding to the brain of the subject, by using such a change model that corresponds to the attribute information of the subject and is selected from among the change models of brain atrophy generated in correspondence with the different pieces of attribute information. For example, the image processing function 172 obtains the attribute information of the subject and obtains an atrophy degree table corresponding to the obtained attribute information. Further, the image processing function 172 obtains the pieces of cerebral gyrus data by dividing the imaged data of the subject into the sections corresponding to the cerebral gyri and performs the atrophying process on each of the pieces of cerebral gyrus data on the basis of the obtained atrophy degree table. In other words, the image processing function 172 renders atrophy caused in the brain region in the imaged data of the subject by using the atrophy parameter calculated from the brain images of the individual persons having the same attribute information as that of the subject. Accordingly, the medical image processing apparatus 1 is able to generate the estimation data that is suited for the attributes of the subject and thus has a higher level of precision. It is therefore possible to extract the site atrophied by a disease more accurately.

<Processing Targets>

In the embodiment described above, the example is explained in which the change models of brain atrophy due to aging are generated by using the brain images of the plurality of healthy people in the large range of ages, so that the process is performed to recognize the brain atrophy caused by a disease, from within brain atrophy of the subject who is suffering from the disease. However, possible embodiments are not limited to this example. It is also acceptable to perform the process while using any other change model. In other words, the image processing function 172 may obtain first imaged data taken of a subject and second imaged data taken of the subject on a date/time different from a date/time on which the first imaged data was taken and may generate estimation data by performing an image processing process that changes the first imaged data on the basis of a predetermined change model. The display image generating function 174 may then generate a display image indicating the difference between the estimation data and the second imaged data.

For example, a process may be performed to judge how a lesion site is progressing after a treatment, on the basis of a change model indicating temporal changes in lesion sites after treatments. In one example, the present disclosure may be applied to a process of judging the post-treatment state of a lesion site having a tumor, an aneurysm, a thrombosis, a stricture, or the like. FIG. 13 is a table illustrating examples of standard data of images taken of lesion sites according to the embodiment. FIG. 13 illustrates an example using tumors. For example, as for the standard data of images each taken of a tumor, the standard data is generated in correspondence with pieces of attribute information including information about the tumors, as illustrated in FIG. 13.

In one example, as illustrated in FIG. 13, the standard data of images taken of lesion sites is generated by using images categorized by the number of days that have passed since a treatment (hereinafter, "the number of elapsed days"), in correspondence with pieces of attribute information including the gender, the age, the type of the tumor, the stage, the treatment method, and the like. In this situation, when lesions are related to tumors, aneurysms, thromboses, strictures, or the like, the shapes and the sizes thereof vary among subjects, even if the type or the stage are the same. Accordingly, it would be difficult to generate a standard tumor image corresponding to each of the numbers of elapsed days. For this reason, as standard data of images each taken of a lesion site, for example, a decrease rate of the volume of a tumor is generated in correspondence with each of the numbers of elapsed days. In other words, a decrease rate of the volume of a tumor is calculated for each of a plurality of subjects with respect to each of the different numbers of days that have passed since the treatment, so that a value averaging the calculated decrease rates for each of the different numbers of elapsed days is generated as the standard data. The standard data corresponding to each of the different numbers of elapsed days is generated in correspondence with each of different pieces of attribute information, as illustrated in FIG. 13. Alternatively, the standard data corresponding to the attribute information illustrated in FIG. 13 may be generated in correspondence with ethnic groups of the subjects, for example.

In one example, with respect to a plurality of subjects corresponding to attribute information such as "ethnic group: B; gender: male; age: 20-29; type of the tumor: C; stage: D; and treatment method: E", a decrease rate of the volume of the tumor is calculated for each of the different numbers of days that have passed since the treatment such as "30 days", "60 days", "90 days" and "120 days". Further, the calculated decreased rates are averaged for each of the different numbers of elapsed days "30 days", "60 days", "90 days", and "120 days", so as to obtain the standard data corresponding to each of the durations. Similarly, standard data is generated for each of the other pieces of attribute information. In the process that uses the change model of tumors, the abovementioned standard data (the decrease rate) corresponding to each of the different numbers of elapsed date is used for generating the estimation data for each of the subjects.

In this situation, the standard data described above may be generated by the medical image processing apparatus 1 by using the tumor images and the attribute information of the subject obtained via the network 41 and may be stored in the storage circuitry 14. In other words, the processing circuitry included in the medical image processing apparatus 1 may generate the standard data corresponding to the attribute information by using the tumor images and the attribute information. Alternatively, the standard data may be generated by the medical information management apparatus 91, obtained by the medical image processing apparatus 1 via the network 41, and stored in the storage circuitry 14. Further, the standard data described above may be updated as appropriate, when the databases in the big data are updated.

The image processing function 172 is configured to generate the estimation data by performing the image processing process that changes the region corresponding to the site of the subject suffering from the disease within the first imaged data, by using such a change model that corresponds to the attribute information of the subject and is selected from among the change models of the disease generated in correspondence with the different pieces of attribute information. For example, the image processing function 172 generates the estimation data of the subject by using the abovementioned standard data (e.g., the data of the decrease rates of the tumors). In one example, the image processing function 172 performs an image processing process of decreasing the volume of the tumor in a tumor image taken immediately before a treatment of a subject having attribute information such as "ethnic group: B, gender: male; age: 20-29; type of the tumor C; stage: D; and treatment method: E" by using the decrease rate corresponding to the number of elapsed days "30 days" for the same attribute information. In this manner, the image processing function 172 generates the estimation data for the subject corresponding to when "30 days" have passed since the treatment. In other words, the image processing function 172 generates a tumor image in which the tumor of the subject is reduced by using the standard decrease rate corresponding to when "30 days" have passed since a treatment.

The display image generating function 174 is configured to generate a display image by performing a subtraction process on the generated estimation data and the imaged data of the subject taken when "30 days" have elapsed. In other words, the display image generating function 174 generates the display image indicating the difference between the tumor image in which the tumor is reduced by the standard decrease rate and the actual tumor image. With this arrangement, it is possible to present, in a visually recognizable manner, how the tumor of the subject is progressing after the treatment compared to the standard progress (e.g., if the tumor is getting smaller quickly or slowly).

In this situation, similarly to the example of the brain image described above, the display image generated by the display image generating function 174 may be an image highlighting the difference by using different color hues, different levels of darkness, or different levels of opacity. Further, in the embodiment described above, tumors are used in the example; however, possible embodiments are not limited to this example. For instance, the present disclosure may also be applied to other lesion sites (e.g., aneurysms, thromboses, strictures, and the like).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image processing apparatus, comprising:
   a memory to store a change model indicating temporal changes in a site;
   processing circuitry configured to
      obtain first imaged data taken of a subject and second imaged data taken of the subject on a second date/time different from a first date/time on which the first imaged data was taken,
      generate estimation image data by performing an image processing process that changes the first imaged data based on the stored change model, and
      generate a lesion change site image indicating a difference between the estimation image data and the second imaged data; and
   a display configured to display the lesion change site image.

2. The medical image processing apparatus according to claim 1, further comprising input circuitry configured to receive an input operation from an operator, wherein the processing circuitry is further configured to generate the estimation image data while changing a change amount in the image processing process in accordance with the input operation.

3. The medical image processing apparatus according to claim 2, wherein the processing circuitry is further configured to perform the image processing process on the first imaged data after changing a parameter used in the image processing process based on the first and second dates/times on which the first imaged data and the second imaged data were taken.

4. The medical image processing apparatus according to claim 1, wherein the image processing process is an image processing process that renders atrophy caused in a region corresponding to a brain of the subject.

5. The medical image processing apparatus according to claim 4, wherein the processing circuitry is further configured to generate the estimation image data by performing the image processing process, which renders the atrophy caused in the region corresponding to the brain within the first imaged data.

6. The medical image processing apparatus according to claim 1, wherein the processing circuitry is further configured to generate the lesion change site image by calculating a difference between the estimation image data and the second imaged data.

7. The medical image processing apparatus according to claim 2, wherein
   the input circuitry is further configured to receive one of an input and a selection of time-series specification information as information specifying an atrophy parameter, which is a parameter used for the image processing process to apply an atrophying process to a brain, and
   the processing circuitry is further configured to obtain the atrophy parameter based on the time-series specification information.

8. The medical image processing apparatus according to claim 1, wherein the processing circuitry is further configured to output a comparison image obtained by comparing the second imaged data taken of a brain of the subject with the estimation image data generated by setting an atrophy parameter, which is a parameter used for the image processing process to apply an atrophying process to the brain so as to coincide with a time period during which the second imaged data was taken.

9. The medical image processing apparatus according to claim 4, wherein the processing circuitry is further configured to generate the estimation image data by applying an atrophying process to the first imaged data with respect to each of cerebral gyri.

10. The medical image processing apparatus according to claim 1, wherein
    the processing circuitry is further configured to generate a display image in which the second imaged data taken of a brain of the subject is displayed side by side with the estimation image data generated by setting an atrophy parameter, which is a parameter used for the image processing process to apply an atrophying process to the brain so as to coincide with a time period during which the second imaged data was taken, and
    the display is configured to display the display image.

11. The medical image processing apparatus according to claim 8, wherein the processing circuitry is further configured to
    generate the comparison image based on the lesion change site image indicating the difference between the second imaged data and the estimation image data, which is generated by setting the atrophy parameter so as to coincide with a time period during which the second imaged data was taken, and further generate a display image containing the comparison image, and cause the display to display the generated display image.

12. The medical image processing apparatus according to claim 8, wherein the processing circuitry is further configured to generate the comparison image displayed in a highlighted manner so that a size of a vector in a warp field is recognizable, based on the warp field, which is generated by using the estimation image data and the second imaged data, generate the display image containing the comparison image, and cause the display to display the generated display image.

13. The medical image processing apparatus according to claim 8, wherein the processing circuitry is further configured to display, in a highlighted manner, an atrophied site in the comparison image by allocating the atrophied site to one or more of divided areas of a brain map.

14. The medical image processing apparatus according to claim 4, wherein the processing circuitry is further configured to perform an erosion process as an atrophying process that renders the atrophy caused in the region corresponding to the brain.

15. The medical image processing apparatus according to claim 4, wherein the processing circuitry is further configured to perform the image processing process, which renders the atrophy caused in the region corresponding to the brain of the subject, by using the change model, which corresponds to attribute information of the subject and is selected from among change models of brain atrophy generated in correspondence with pieces of attribute information.

16. The medical image processing apparatus according to claim 1, wherein the processing circuitry is further configured to generate the estimation data by performing the image processing process, which changes a region corresponding to a site of the subject suffering from a disease within the first imaged data, by using the change model, which corresponds to attribute information of the subject and is selected from among change models of the disease generated in correspondence with pieces of attribute information.

* * * * *